US011969437B2

(12) United States Patent
Endo et al.

(10) Patent No.: US 11,969,437 B2
(45) Date of Patent: Apr. 30, 2024

(54) ALGINATE LIQUID PREPARATION (71) Applicant: MOCHIDA PHARMACEUTICAL CO., LTD., Tokyo (JP)

(72) Inventors: Shuichi Endo, Tokyo (JP); Motoi Nakahara, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/491,709

(22) PCT Filed: Mar. 6, 2018

(86) PCT No.: PCT/JP2018/008592
§ 371 (c)(1),
(2) Date: Sep. 6, 2019

(87) PCT Pub. No.: WO2018/164128
PCT Pub. Date: Sep. 13, 2018

(65) Prior Publication Data
US 2020/0069726 A1   Mar. 5, 2020

(30) Foreign Application Priority Data
Mar. 7, 2017   (JP) ................. 2017-043095

(51) Int. Cl.
*A61K 31/734* (2006.01)
*A61K 9/08* (2006.01)
*A61K 47/02* (2006.01)

(52) U.S. Cl.
CPC .............. *A61K 31/734* (2013.01); *A61K 9/08* (2013.01); *A61K 47/02* (2013.01)

(58) Field of Classification Search
CPC ......... A61K 31/734; A61K 9/08; A61K 47/02
See application file for complete search history.

(56) References Cited

U.S. PATENT DOCUMENTS

| | | |
|---|---|---|
| 5,589,591 A | 12/1996 | Lewis |
| 6,451,772 B1 | 9/2002 | Bousman et al. |
| 8,927,524 B2 | 1/2015 | Bender et al. |
| 2010/0015102 A1 | 1/2010 | Iwasaki et al. |
| 2010/0136140 A1 | 6/2010 | Zhao |
| 2010/0298262 A1 | 11/2010 | Basta et al. |
| 2011/0130473 A1 | 6/2011 | Fuchs et al. |
| 2013/0096080 A1 | 4/2013 | Bender et al. |
| 2013/0189231 A1 | 7/2013 | Iwasaki et al. |
| 2014/0018315 A1 | 1/2014 | Fuchs et al. |
| 2014/0275519 A1 | 9/2014 | Basta et al. |
| 2015/0250165 A1 | 9/2015 | Balastre et al. |
| 2015/0352144 A1* | 12/2015 | Cohen ................. A61K 31/734 514/54 |
| 2016/0095962 A1 | 4/2016 | Fukuda et al. |
| 2018/0142041 A1 | 5/2018 | Fuchs et al. |
| 2018/0338921 A1 | 11/2018 | Endo et al. |
| 2019/0083678 A1 | 3/2019 | Suzuki et al. |

FOREIGN PATENT DOCUMENTS

| | | |
|---|---|---|
| CN | 101835501 A | 9/2010 |
| EP | 0 867 453 A2 | 9/1998 |
| JP | 63-132833 A | 6/1988 |
| JP | 2-172913 A | 7/1990 |
| JP | 8-269102 A | 10/1996 |
| JP | 9-324001 A | 12/1997 |
| JP | 11-5743 A | 1/1999 |
| JP | 2002-530440 A | 9/2002 |
| JP | 2005-36036 A | 2/2005 |
| JP | 3796165 A | 7/2006 |
| JP | 2010-90052 A | 4/2010 |
| JP | 2010-514707 A | 5/2010 |
| JP | 2011-503047 A | 1/2011 |
| JP | 5684575 B2 | 3/2015 |
| JP | 2016-187328 A | 11/2016 |
| WO | WO 93/13136 A1 | 7/1993 |
| WO | WO 00/29449 A1 | 5/2000 |
| WO | WO 2008/102855 A1 | 8/2008 |

(Continued)

OTHER PUBLICATIONS

ASTM F2064-00, "Standard Guide for Characterization and Testing of Alginates as Starting Materials Intended for Use in Biomedical and Tissue-Engineered Medical Products Application", published by ASTM International, 2006, pp. 1074-1081.
FMC Biopolymer, PRONOVA™ sodium alginates catalogue, 2002, total 3 pages.
International Search Report, issued in PCT/JP2018/008592, dated Jun. 5, 2018.
Kagaku Kogyo Magazine, 1958, vol. 61, No. 7, pp. 874-877.
Kagaku Kogyo Magazine, 1958, vol. 61, No. 7, pp. 871-874.
Polyzois et al., "Stability of some soluble alginate solutions", Biomaterials, 1985, vol. 6, pp. 68-69.
Sato et al., "On the Improvements in Manufacturing of Alginic Acid (4) Study on Viscosity Deterioration of Sodium Alginate Owing to Heating", Muroran Institute of Technology Research Report, 1957, vol. 2, No. 3, pp. 609-616.

(Continued)

*Primary Examiner* — Pancham Bakshi
(74) *Attorney, Agent, or Firm* — Birch, Stewart, Kolasch & Birch, LLP (57) ABSTRACT

The present invention provides a ready-to-use sterile alginate aqueous solution preparation which is packed in a sealed container or an airtight container and which has storage stability, comprising: (a) a low-endotoxin monovalent metal salt of alginic acid having a weight average molecular weight of 50,000 to 400,000 by a GPC-MALS method; (b) a salt selected from a monovalent metal salt and an ammonium salt; and (c) water, wherein a concentration of the component (a) is 1.5% by mass or more, a concentration of the component (b) is 0.5 to 2% by mass, and a viscosity measured at 20° C. using a rotational viscometer is 2700 mPa·s or more, and a method of producing the same. This alginate aqueous solution preparation is a ready-to-use aqueous solution preparation of a low-endotoxin monovalent metal salt of alginic acid.

11 Claims, 4 Drawing Sheets

(56) References Cited

FOREIGN PATENT DOCUMENTS

| WO | WO 2009/054181 A1 | 4/2009 |
| WO | WO 2014/192807 A1 | 12/2014 |
| WO | WO 2016/114355 A1 | 7/2016 |
| WO | WO 2017/043485 A1 | 3/2017 |
| WO | WO 2017/159700 A1 | 9/2017 |
| WO | WO 2017/163603 A1 | 9/2017 |

OTHER PUBLICATIONS

Sato et al., "On the Improvements in Manufacturing of Alginic Acid (6) Study of Viscosity Deterioration of Free Alginic Acid by Heating", Muroran Institute of Technology Research Report, 1960, vol. 3, No. 3, pp. 443-449.

Written Opinion of the International Searching Authority, issued in PCT/JP2018/008592, dated Jun. 5, 2018.

Yokota et al., "Pyruvic acid production by a lipoic acid auxotroph of *Escherichia coli* W1485", Appl Microbiol Biotechnol, 1994, vol. 41, pp. 638-643.

Yomota et.al., "Evaluation of Molecular Weight of Hyaluronate Preparations by Size-exclusion Chromatography", Bull. Natl. Health Sci., 1999, vol. 117, pp. 135-139.

Yomota, "Evaluation of Molecular Weights of Hyaluronate Preparations by Multi-Angle Laser Light Scattering", Bull. Natl. Inst. Health Sci., 2003, vol. 121, pp. 30-33.

Extended European Search Report dated Nov. 18, 2020, in European Patent Application No. 18763932.3.

Chinese Office Action for Appl. No. 201880016492.X dated Jul. 18, 2022.

Pan, Wei-San, "Planned Teaching Materials Round 4 of Pharmaceuticals of Countrywide Medical Colleges and Universities, For majoring in pharmaceutical preparation, pharmaceutical engineering, biopharmaceuticals, traditional Chinese medicine, and pharmacy," China Medical Science and Technology Press, Industrial Pharmaceuticals (3rd edition), p. 100, Aug. 2015.

Zhang Yang, et al., "Effect of Electrolyte on the Rheological Behaviors of Sodium Alginate Solutions," Journal of Qingdao University (Natural Science Edition) 26(2), p. 57-61, May 2013, May 31, 2013.

\* cited by examiner

FIG.1

CHANGE WITH LAPSE OF TIME OF VISCOSITY OF SODIUM ALGINATE LIQUID PREPARATION

STABILITY OF 2% SOLUTION OF SODIUM ALGINATE
VISCOSITY (2%)

ALGINATE LIQUID PREPARATION

TECHNICAL FIELD

The present invention relates to an aqueous solution preparation of a monovalent metal alginate useful as a pharmaceutical or medical device, in particular an aqueous solution preparation of a low-endotoxin monovalent metal salt of alginic acid having a weight average molecular weight of 50,000 to 400,000 by a GPC-MALS method, an aqueous solution preparation of a monovalent metal alginate whose viscosity measured at 20° C. using a rotational viscometer is 2700 mPa·s or more, an aqueous solution preparation of a monovalent metal alginate with suppressed viscosity decrease with the lapse of time, an in-vial aqueous solution preparation of a monovalent metal alginate, a ready-to-use aqueous solution preparation of a monovalent metal alginate, an aqueous solution preparation of a monovalent metal alginate having storage stability, a sterile aqueous solution preparation of a monovalent metal alginate, an aqueous solution preparation of a monovalent metal alginate packed in a sealed container or an airtight container, a pre-filled syringe filled with an aqueous solution preparation of a monovalent metal alginate, a method of producing the same, a suppressant of viscosity decrease with the lapse of time for an aqueous solution preparation of a monovalent metal alginate, a method of suppressing viscosity decrease with the lapse of time of an aqueous solution preparation of a monovalent metal alginate, and a method of stabilizing an aqueous solution preparation of a monovalent metal alginate.

BACKGROUND ART

It is known to inject a cartilage defect portion in an articular cartilage with an aqueous solution in which a freeze-dried preparation of monovalent metal alginate such as a freeze-dried sodium alginate (hereinafter also expressed as Na alginate) preparation is dissolved in water, thereby regenerating and treating the cartilage (Patent Literature 1).

Meanwhile, industrial sodium alginate contains sodium chloride, sodium sulfate, sodium hydroxide, sodium carbonate, and the like as impurity electrolytes. It has been investigated that the impurity electrolytes can be removed using a property of being extracted by an alcohol of about 40% or more and that properties such as viscosity, pH, structural viscosity, flow curve, and capillary action change in the case of adding sodium chloride or sodium sulfate to the sodium alginate aqueous solution (Non Patent Literatures 1 and 2).

In addition, a study was carried out on the viscosity decrease attributed to the heating of sodium alginate in the forms of powder and solution. As a result, it has been reported that although viscosity decreases due to heating in both cases, the solution form has a larger viscosity decrease rate (Non Patent Literatures 3 and 4).

Moreover, it has been reported that the addition of sodium citrate to a sodium alginate solution suppresses the viscosity decrease with the lapse of time of the sodium alginate solution (Non Patent Literature 5).

Regarding sodium alginate aqueous solutions, there has been sold a peptic ulcer agent Alloid G Oral Solution 5% whose sodium alginate content is 5% by mass and which contains sodium copper chlorophyllin, sodium dehydroacetate, a paraben, sodium saccharin, ethanol, and a flavor. In addition, Patent Literature 2 discloses a method of obtaining an alginate solution having 20 EU/g or less of endotoxin, and discloses, as preparation of a 1.8% AG solution, that low-viscosity alginate powder (sodium salt of alginic acid (E400)) was added with a physiological solution (0.9% NaCl), followed by stirring to prepare a 1.8% AG solution. Similarly, Patent Literature 3 discloses that a polysaccharide (for example, an alginate) was dissolved in a physiological solution (0.15 M NaCl in water), followed by vigorous stirring with a homogenizer to prepare an alginate sample containing 2% (w/v) alginate, and that the sample was sterilized by filtering with a 0.2 μm nylon membrane. The alginates used here are ones having VLVG (very low viscosity) and LVG (low viscosity). Moreover, Patent Literature 4 discloses use of a hypertonic solution composition for manufacturing medicaments for use during a perioperative period to promote healing of operative wounds or anastomotic stoma, and discloses a hypertonic solution composition containing 3% to 18% (w/v) sodium alginate having a molecular weight of 20,000 to 26,000, 1.5% (w/v) or more of sodium chloride, sodium ions at a concentration of 6.9% (w/v), and a balance amount of conventional injection liquid. Patent Literature 5 discloses a sterilized aqueous composition containing 0.5 to 10 wt % of alginate and a dissolved C2-7 mono- or di-carboxylate, and having a viscosity at 25° C. of at least 300 cp and a pH of 6.5 to 7.5. In its Examples, 0.8% by mass of sodium chloride was added.

CITATION LIST

Patent Literatures

Patent Literature 1: WO 2008/102855
Patent Literature 2: JP 5684575B
Patent Literature 3: US20150352144A
Patent Literature 4: JP 2010-514707A
Patent Literature 5: U.S. Pat. No. 8,927,524B

Non Patent Literatures

Non Patent Literature 1: Kagaku Kogyo Magazine vol. 61, No. 7, 1958 pp. 871-874
Non Patent Literature 2: Kagaku Kogyo Magazine vol. 61, No. 7, 1958 pp. 874-877
Non Patent Literature 3: Muroran Institute of Technology Research Report, 1957, Vol. 2, No. 3, pp. 609-616
Non Patent Literature 4: Muroran Institute of Technology Research Report, 1960, Vol. 3, pp. 443-449
Non Patent Literature 5: Biomaterials 1985 Vol. 6 pp. 68-69

SUMMARY OF INVENTION

The object of the present invention is to provide an aqueous solution preparation of a low-endotoxin monovalent metal salt of alginic acid. More preferably, the object of the present invention is to provide an aqueous solution preparation of a low-endotoxin monovalent metal salt of alginic acid with suppressed viscosity decrease with the lapse of time.

The object of the present invention is to provide an in-vial aqueous solution preparation of a low-endotoxin monovalent metal salt of alginic acid. More preferably, the object of the present invention is to provide an in-vial aqueous solution preparation of a low-endotoxin monovalent metal salt of alginic acid with suppressed viscosity decrease with the lapse of time.

The object of the present invention is to provide a ready-to-use aqueous solution preparation of a low-endotoxin monovalent metal salt of alginic acid More preferably, the present invention aims to provide a ready-to-use aqueous solution preparation of a low-endotoxin monovalent metal salt of alginic acid with suppressed viscosity decrease with the lapse of time.

The object of the present invention is to provide a sterile aqueous solution preparation of a low-endotoxin monovalent metal salt of alginic acid. More preferably, the object of the present invention is to provide a sterile aqueous solution preparation of a low-endotoxin monovalent metal salt of alginic acid with suppressed viscosity decrease with the lapse of time.

The object of the present invention is to provide an aqueous solution preparation of a low-endotoxin monovalent metal salt of alginic acid packed in a sealed container or an airtight container. More preferably, the object of the present invention is to provide an aqueous solution preparation of a low-endotoxin monovalent metal salt of alginic acid with suppressed viscosity decrease with the lapse of time, which is packed in a sealed container or an airtight container.

The object of the present invention is to provide a pre-filled syringe filled with an aqueous solution preparation of a low-endotoxin monovalent metal salt of alginic acid. More preferably, the object of the present invention is to provide a pre-filled syringe filled with an aqueous solution preparation of a low-endotoxin monovalent metal salt of alginic acid with suppressed viscosity decrease with the lapse of time.

The object of the present invention is to provide an efficient method of producing an aqueous solution preparation of a low-endotoxin monovalent metal salt of alginic acid with suppressed viscosity decrease with the lapse of time.

The object of the present invention is to provide a suppressant of viscosity decrease with the lapse of time for an aqueous solution preparation of a low-endotoxin monovalent metal salt of alginic acid.

The object of the present invention is to provide a method of suppressing viscosity decrease with the lapse of time of an aqueous solution preparation of a low-endotoxin monovalent metal salt of alginic acid.

The object of the resent invention is to provide a method of stabilizing an aqueous solution preparation of a low-endotoxin monovalent metal salt of alginic acid.

In order to make a pharmaceutical or medical device directly injected into a living body such as a cartilage regeneration agent into a ready-to-use preparation, the preparation needs to be sterile. When an aqueous solution preparation of a monovalent metal alginate is sterilized by heating or sterilized by electron beams or the like for the purpose of sterilization to obtain an aqueous solution preparation of a low-endotoxin monovalent metal salt of alginic acid, a reduction in molecular weight and a decrease in viscosity of the alginic acid occur, which is not preferable. Meanwhile, in order to aseptically filter (0.22 um filter) a high-viscosity aqueous solution of alginic acid used as, for example, a cartilage regenerating agent, it is necessary to apply a high pressure or it takes a long period of time for filtration, and both cases are not preferable from industrial and other viewpoints. In addition, in the case of, for example, using a solid preparation of a monovalent metal alginate such as a freeze-dried preparation by dissolution at the time of use, appropriate device and facilities such as clean benches may be necessary for the purpose of maintaining sterility, and dissolution may require time for the purpose of obtaining a uniform high-concentration solution of a monovalent metal alginate. Thus, there is a demand for more convenient preparations.

In view of the above, the present inventors have made earnest studies on a method of obtaining a ready-to-use aqueous solution preparation of a low-endotoxin monovalent metal salt of alginic acid, and have found as a result that, surprisingly, by first preparing a low-concentration aqueous solution of a monovalent metal alginate, dissolving a predetermined amount of a salt selected from a monovalent metal salt and an ammonium salt to the resultant, aseptically filtering the obtained aqueous solution, filling a vial, and concentrating the concentration of the monovalent metal alginate by drying under a non-oxidizing atmosphere in a usual manner such as reduced pressure drying, it is possible to obtain an aqueous solution of a low-endotoxin monovalent metal salt of alginic acid being an aqueous solution preparation with suppressed viscosity decrease, and it is possible to efficiently suppress viscosity decrease with the lapse of time of this aqueous solution preparation. Based on these findings, the present invention has been completed.

Alternatively, it was confirmed that, also by preparing a low-concentration aqueous solution of a monovalent metal alginate, dissolving a predetermined amount of a salt selected from a monovalent metal salt and an ammonium salt to the resultant, aseptically filtering the obtained aqueous solution, concentrating the aqueous solution of a monovalent metal alginate by drying under a non-oxidizing atmosphere in a usual manner such as reduced pressure drying prior to filling a container such as a vial or a syringe, and then filling the container for sealing, it is possible to obtain an intended aqueous solution of a low-endotoxin monovalent metal salt of alginic acid being an aqueous solution preparation with suppressed viscosity decrease, and it is possible to efficiently suppress viscosity decrease with the lapse of time of this aqueous solution preparation.

To be more specific, the present invention has the following aspects achieving the above objects.

(1-1) A ready-to-use sterile alginate aqueous solution preparation which is packed in a sealed container or an airtight container and which has storage stability, comprising: (a) a low-endotoxin monovalent metal salt of alginic acid having a weight average molecular weight of 50,000 to 400,000 by a GPC-MALS method; (b) a salt selected from a monovalent metal salt and an ammonium salt; and (c) water, wherein a concentration of the component (a) is 1.5% by mass or more, a concentration of the component (b) is 0.5 to 2% by mass, and a viscosity measured at 20° C. using a rotational viscometer is 2700 mPa·s or more.

(1-2) The alginate aqueous solution preparation of (1-1), wherein the salt selected from a monovalent metal salt and an ammonium salt is a water-soluble inorganic salt.

(1-3) The alginate aqueous solution preparation of (1-1) or (1-2), wherein the salt selected from a monovalent metal salt and an ammonium salt is sodium chloride.

(1-4) The alginate aqueous solution preparation of (1-1) to (1-3), wherein the sealed container or the airtight container is a vial.

(1-5) A pre-filled syringe of the alginate aqueous solution preparation of (1-1) or (1-3), wherein the sealed container or the airtight container is a syringe.

(1-6) The alginate aqueous solution preparation of any one of (1-1) to (1-5), consisting of the components (a), (b), and (c).

(1-7) The alginate aqueous solution preparation of any one of (1-1) to (1-6), wherein a three-month viscosity decrease rate of the preparation having storage stability satisfies any of 1) less than 3% in a case of storage at 2 to 8° C.,
2) less than 7% in a case of storage at 25° C., and
3) less than 47% in a case of storage at 40° C.

(1-8) The alginate aqueous solution preparation of any one of (1-1) to (1-7) for use as a pharmaceutical or medical device.

(1-9) The alginate aqueous solution preparation of any one of (1-1) to (1-8), wherein a volume of the sealed container or the airtight container is 2 to 50 ml.

(1-10) The alginate aqueous solution preparation of any one of (1-1) to (1-9), wherein a filling amount of an alginate aqueous solution into the sealed container or the airtight container is 5 to 20 ml.

(1-11) The alginate aqueous solution preparation of any one of (1-1) to (1-10), wherein the filling amount of an alginate into the sealed container or the airtight container is, as dry sodium alginate, 50 to 500 mg.

(1-12) The alginate aqueous solution preparation of any one of (1-9) to (1-11), wherein the sealed container or the airtight container is a vial.

(1-13) A pre-filled syringe of the alginate aqueous solution preparation of (1-9) to (1-11), wherein the sealed container or the airtight container is a syringe.

(1-14) The alginate aqueous solution preparation of any one of (1-1) to (1-13), wherein air in the sealed container or the airtight container is replaced by nitrogen gas.

(1-15) The alginate aqueous solution preparation of (1-14), wherein the sealed container or the airtight container is a vial.

(1-16) The alginate aqueous solution preparation of (1-14), wherein the sealed container or the airtight container is a syringe.

(2-1) A method of producing the alginate aqueous solution preparation of any one of (1-1) to (1-16), comprising: sterilically or aseptically filtering an aqueous solution of a monovalent metal alginate containing a salt selected from a monovalent metal salt and an ammonium salt, filling a container with the filtrate, followed by sealing after concentrating the filtrate; or after freeze-drying the filtrate and aseptically reconstituting the freeze-dried one with water.

(2-2) The method of producing an alginate aqueous solution preparation of (2-1), wherein the container is a vial.

(2-3) A method of producing the alginate aqueous solution preparation of any one of (1-1) to (1-16), comprising: sterilically or aseptically filtering an aqueous solution of a monovalent metal alginate containing a salt selected from a monovalent metal salt and an ammonium salt; concentrating the filtrate and aseptically filling a container with the concentrated filtrate, followed by sealing.

(2-4) The method of producing an alginate aqueous solution preparation of (2-3), wherein the sealed container or the airtight container is a vial.

(2-5) The method of producing a pre-filled syringe of an alginate aqueous solution preparation of (2-3), wherein the container is a syringe.

(3-1) A suppressant of viscosity decrease with the lapse of time for an aqueous solution preparation of a monovalent metal alginate, comprising: a salt selected from a monovalent metal salt and an ammonium salt as an active ingredient.

(4-1) A method of suppressing viscosity decrease with the lapse of time of an aqueous solution preparation of a monovalent metal alginate, comprising: incorporating a salt selected from a monovalent metal salt and an ammonium salt into an aqueous solution of a monovalent metal alginate.

(5) A ready-to-use sterile vial which has storage stability and which is filled with an alginate aqueous solution comprising: (a) a low-endotoxin monovalent metal salt of alginic acid having a weight average molecular weight of 50,000 to 400,000 by a GPC-MALS method; (b) a salt selected from a monovalent metal salt and an ammonium salt; and (c) water, wherein a concentration of the component (a) is 1.5% by mass or more, a concentration of the component (b) is 0.5 to 2% by mass, and a viscosity measured at 20° C. using a rotational viscometer is 2700 mPa·s or more.

(6) A composition being a ready-to-use sterile alginate aqueous solution which has storage stability and which is packed in a sealed container or an airtight container, comprising: (a) a low-endotoxin monovalent metal salt of alginic acid having a weight average molecular weight of 50,000 to 400,000 by a GPC-MALS method; (b) a salt selected from a monovalent metal salt and an ammonium salt; and (c) water, wherein a concentration of the component (a) is 1.5% by mass or more, a concentration of the component (b) is 0.5 to 2% by mass, and a viscosity measured at 20° C. using a rotational viscometer is 2700 mPa·s or more.

The present invention makes it possible to provide an aqueous solution preparation of a monovalent metal alginate which can efficiently suppress viscosity decrease with the lapse of time of a monovalent metal alginate in the aqueous solution preparation of a monovalent metal alginate even in the case of long-term storage or preservation. Further, present invention employs the step of aseptically filtering an aqueous solution formed by dissolving the component (a) and the component (b), followed by drying under a non-oxidizing atmosphere to concentrate the concentration of the monovalent metal alginate, thereby making it possible to enjoy an industrial advantage that it is possible to obtain an aqueous solution of a low-endotoxin monovalent metal salt of alginic acid being an aqueous solution preparation with suppressed viscosity decrease, and to efficiently suppress viscosity decrease with the lapse of time of this aqueous solution preparation.

DESCRIPTION OF EMBODIMENTS

Alginic acid, which is a constituent component of a monovalent metal alginate (a) used in the present invention, is a natural polysaccharide which is produced by extraction from seaweed followed by purification. In addition, alginic acid is a polymer formed by polymerization of D-mannuronic acid (M) and L-guluronic acid (G). A method of industrially producing alginic acid includes, for example, the acid method and the calcium method. In the present invention, it is possible to use alginic acid produced by any of these methods, and the quantitative value determined by purification and the HPLC method is preferably within a range of 90 to 110% by mass. Commercially available products that can be purchased and utilized include products marketed by KIMICA Corporation as KIMICA ALGIN series, preferably products of fine food & pharmaceutical grades. It is possible to use commercially available products after further purification as appropriate.

The monovalent metal alginate used in the present invention is preferably one in which the hydrogen cations of carboxyl groups of alginic acid are ion-exchanged with monovalent metal cations such as sodium and potassium, particularly alkali metal cations. Among these, sodium alginate, potassium alginate, a mixture of these, or the like is preferable, and sodium alginate is particularly preferable.

The monovalent metal alginate used in the present invention is one having a weight average molecular weight of 50,000 to 400,000 by the GPC-MALS method. Among these, one having a weight average molecular weight of 100,000 to 400,000 is preferable. Here, one whose upper limit of the weight average molecular weight is 300,000 is further preferable.

In general, a polymer substance of natural origin does not have a single molecular weight. Since the polymer substance of natural origin is a collection of molecules having various molecular weights, it is measured as a molecular weight distribution having a certain width. A representative measuring method is gel filtration chromatography. The representative information on the molecular weight distribution obtained by gel filtration chromatography includes the weight average molecular weight (Mw), the number average molecular weight (Mn), and the dispersion ratio (Mw/Mn).

The weight average molecular weight places importance on the contribution of polymers having large molecular weights to the average molecular weight and is expressed by the following equation.

$$Mw=\Sigma(WiMi)/W=\Sigma(HiMi)/\Sigma(Hi)$$

The number average molecular weight is calculated by dividing the total weight of the polymer by the total number of the polymers:

$$Mn=W/\Sigma Ni=\Sigma(MiNi)/\Sigma Ni=\Sigma(Hi)/\Sigma(Hi/Mi),$$

where W is the total weight of the polymer, Wi is the weight of the i-th polymer, Mi is the molecular weight in the i-th elution time, Ni is the number of the molecular weights Mi, and Hi is the height in the i-th elution time.

It is known that in the molecular weight measurement of a polymer substance of natural origin, the values can differ depending on the measurement method (examples of hyaluronic acid: Chikako YOMOTA et. al. Bull. Natl. Health Sci., Vol. 117, pp 135-139 (1999), Chikako YOMOTA et. al. Bull. Natl. Inst. Health Sci., Vol. 121, pp 30-33 (2003)).

Regarding the molecular weight measurement of an alginate, there is a literature (ASTM F2064-00 (2006), published by ASTM International) which describes a calculation method starting from intrinsic viscosity and a calculation method by SEC-MALLS (size exclusion chromatography with multiple angle laser light scattering detection). Note that when measuring the molecular weight by size exclusion chromatography (=gel filtration chromatography), this literature states that it is insufficient only to perform calculation with a calibration curve using pullulan as a standard substance and recommends to also use a multiple angle laser light scattering (MALLS) detector (=measurement by SEC-MALLS). Therefore, the present invention employs the weight average molecular weights (Mw) of alginates by SEC-MALLS (FMC Biopolymer, PRONOVA™ sodium alginates catalogue). Here, SEC-MALLS is a method of determining the absolute molecular weight of a polymer by connecting a multiple angle light scattering (MALS) detector to GPC (SEC).

Thus, in the case of identifying the molecular weight of an alginate in the present specification, the molecular weight in consideration is the weight average molecular weight calculated by SEC-MALLS (GPC-MALS method) unless otherwise noted. Preferable conditions of SEC-MALLS involve, for example, use of a calibration curve with pullulan as a standard substance. The molecular weight of pullulan used as a standard substance is preferably at least 1,600,000, 788,000, 404,000, 212,000, and 112,000. In addition to the above, it is possible to determine eluent (200 mM solution of sodium nitrate), column condition, and the like. As the column condition, it is preferable to use a polymethacrylate resin-based packing material and to use at least one column having an exclusion limit molecular weight of 10,000,000 or more. A representative column is TSKgel GMPWxl (diameter of 7.8 mm×300 mm) (manufactured by Tosoh Corporation).

In addition, for example, as the monovalent metal alginate used in the present invention, the viscosity of 1% liquid (20° C.) measured using a rotational viscometer by the viscosity measuring method conforming to the Japanese Pharmacopoeia is preferably 50 to 20,000 mPa·s, more preferably 50 to 10,000 mPa·s, more preferably 100 to 5,000 mPa·s, more preferably 300 to 800 mPa·s, and further preferably 300 to 600 mPa·s. In addition, preparations ready-to-use as pharmaceuticals or medical device include, for example, ones whose viscosity (20° C.) measured using a rotational viscometer by the viscosity measuring method conforming to the Japanese Pharmacopoeia is preferably 2700 mPa·s or more, more preferably 3000 mPa·s or more, and further preferably 3300 mPa·s or more.

In addition, the monovalent metal alginate used in the present invention is recommended to be one having an appropriate M/G ratio depending on the end use purpose. It is preferable to use one having an M/G ratio of preferably 0.4 to 2.0, more preferably 0.6 to 1.8, and further preferably 0.8 to 1.6. Monovalent metal alginates having these M/G ratios are useful in the treatment of cartilage disorder.

In addition, the monovalent metal alginate used in the present invention is recommended to be one having a reduced endotoxin level. The endotoxin value measured by the endotoxin test conforming to the Japanese Pharmacopoeia is preferably less than 100 EU/g, more preferably less than 75 EU/g, and further preferably less than 50 EU/g. Such reduction in endotoxin level can be carried out by a known method or a similar method. For example, reduction can be carried out using the method by Kan et al. of purifying sodium hyaluronate (see, for example, JP 9-324001A and the like), the method by Yoshida et al. of purifying β1,3-glucan (see, for example, JP 8-269102A and the like), the method by William et al. of purifying a biopolymer salt such as an alginate and gellan gum (see, for example, Published Japanese Translation of JP 2002-530440A and the like), the method by James et al. (see, for example, WO 93/13136 and the like) and the method by Lewis et al. (see, for example, U.S. Pat. No. 5,589,591 and the like) of purifying a polysaccharide, the method by Hermann Frank et al. of purifying an alginate (see, for example, Appl Microbiol Biotechnol (1994) 41: 638-643 and the like), and the like, or using similar methods. The low endotoxin treatment of the present invention is not limited thereto, and can be carried out by a known method such as washing, filtration with a filter (such as an endotoxin removal filter or a charged filter), ultrafiltration, purification using a column (such as an endotoxin adsorption affinity column, a gel filtration column, or a column by ion exchange resin), adsorption to a hydrophobic substance, a resin, activated carbon, or the like, organic solvent treatment (such as extraction with an organic solvent or precipitation/sedimentation by the addition of an organic solvent), surfactant treatment (see, for example, JP 2005-036036A and the like), or the like, or by a combination of these as appropriate. The steps of these processes may appropriately be combined with known methods such as centrifugation. It is desirable to appropriately make selection according to the type of alginic acid and the like.

The monovalent metal salt and the ammonium salt used as the component (b) of the present invention include a water-soluble inorganic salt. Among these, as the monovalent metal salt, it is preferable to use a salt of monovalent metal such as sodium and potassium, in particular a water-soluble salt of alkali metal. To be more specific, the inorganic salt includes, for example, a hydrochloride, a sulfate, and a nitrate of an alkali metal. Among these, a hydrochloride is preferable, and sodium chloride and potassium chloride are particularly preferable. Sodium chloride is most preferable.

In addition, a preferable ammonium salt includes water-soluble ammonium chloride and the like.

In the present invention, the mass ratio of the component (a)/the component (b) is preferably 100/70 to 100/10, more preferably 100/60 to 100/20, and most preferably 100/about 45. If the component (b) is sodium chloride, it is preferable to blend the component (a) with the component (b) so that the concentration of sodium chloride in the ready-to-use preparation is equivalent to that of physiological saline.

In the alginate aqueous solution preparation of the present invention, the concentration of the component (a) is 1.5% by mass or more and the concentration of the component (b) is 0.5 to 2% by mass. Here, the preferable concentration of the component (a) depends on the molecular weight of alginic acid used, and in the case of using ALG-1 (having an average molecular weight by the GPC-MALS method of 250,000) mentioned in Examples to be described later, the concentration is preferably 1.5% by mass to 3% by mass, more preferably 1.8% by mass to 2.5% by mass, and most preferably 2% by mass. In the case of using ALG-2 (having an average molecular weight by the GPC-MALS method of 150,000) mentioned in Examples to be described later, the concentration is preferably 2% by mass to 5% by mass, more preferably 2.5% by mass to 4% by mass, and most preferably 3.5% by mass. In the case of using an alginic acid having an average molecular weight by the GPC-MALS method of 72,000, the concentration is preferably 3% by mass to 7% by mass, more preferably 4% by mass to 6% by mass, and most preferably 4.5 to 5% by mass.

In addition, the concentration of the component (b) is preferably 0.5 to 2% and more preferably 0.9%.

The alginate aqueous solution preparation of the present invention can contain sugars such as mannitol, xylitol, and white soft sugar as additional components as long as the performance thereof is not impaired, but preferably contain only the component (a), the component (b), and water (c). Meanwhile, it is preferable that the alginate aqueous solution preparation of the present invention does not contain a C2-7 mono- or dicarboxylate. In addition, it is preferable that the alginate aqueous solution preparation of the present invention does not contain sodium citrate. In addition, it is preferable that the alginate aqueous solution preparation of the present invention does not contain a calcium salt. In addition, it is preferable that the alginate aqueous solution preparation of the present invention does not contain a cross-linked alginate.

The water used here is preferably injection water.

The viscosity of the alginate aqueous solution preparation of the present invention usually indicates a value of 2700 mPa·s or more, preferably indicates a value of 3000 mPa·s or more, and more preferably indicates a value of 3300 mPa·s or more.

The viscosity of the alginate aqueous solution preparation of the present invention can be measured according to a conventional method. For example, measurement can be carried out using a coaxial double cylindrical rotational viscometer, a single cylindrical rotational viscometer (Brookfield viscometer), a cone-plate rotational viscometer (cone plate viscometer), or the like of the rotational viscometer method. The measurement preferably conforms to the viscosity measuring method of the Japanese Pharmacopoeia (Sixteenth Edition). In the present invention, it is desirable to measure the viscosity under the condition of 20° C. For example, in the case of measurement using a cone plate viscometer, the measurement can be carried out under the following measurement conditions. The sample solution is prepared using MilliQ water. The measurement temperature is 20° C. The rotational speed of the cone plate viscometer is determined by using 1 rpm for the measurement of a 1% solution of monovalent metal alginate and 0.5 rpm for the measurement of a 2% solution, and using these as a standard. The reading time for measurement is 2 minutes in the case of measuring a 1% solution of monovalent metal alginate, and the average value employed is the average during the interval between 1 minute after the start and until 2 minutes after the start. Measurement is carried out for 2.5 minutes in the case of a 2% solution, and the average value employed is the average during the interval between 0.5 minutes after the start and until 2.5 minutes after the start. The test value is the average of three measurements.

As mentioned in the Examples to be described later, the measurement of the viscosity in the present invention was carried out on the viscosity at 20° C. for 3 minutes by use of a two-axis cylindrical metal cup in a rotational viscometer RheoStress RS600 (manufactured by Thermo Haake GmbH), and the measurement value employed was the average during the interval between 1 minute after the start and until 2 minutes after the start.

The alginate aqueous solution preparation of the present invention is preferably kept in cold storage, preferably at 2 to 8° C. Preservation in cold storage suppresses the decomposition of the monovalent metal alginate and suppresses viscosity decrease. The alginate aqueous solution preparation of the present invention preferably has a shelf life or expiration limit of 2 years or 3 years storing at 2 to 8° C. The viscosity decrease rate after storage of the alginate aqueous solution preparation of the present invention at 2 to 8° C. for 2 years is usually less than 40%, preferably less than 30%, and further preferably less than 20%. The viscosity decrease rate can be extrapolated with accelerated test results, statistical processing, and the like.

The alginate aqueous solution preparation of the present invention preferably has storage stability. In the present invention, the phrase having storage stability means that the viscosity decrease rate after storage of the preparation for three months under the following conditions satisfies any of the following 1) less than 3% in the case of storage at 2 to 8° C.,
2) less than 7% in the case of storage at 25° C. and a humidity of 60%, and
3) less than 47% in the case of storage at 40° C. and a humidity of 75%.

Note that the viscosity decrease rate after storage for 3 months in the case of storage at 2 to 8° C. is preferably less than 2% and more preferably less than 1.5%, the viscosity decrease rate after storage for 3 months in the case of storage at 25° C. and a humidity of 60% is preferably less than 6% and more preferably less than 5%, and the viscosity decrease rate after storage for 3 months in the case of storage at 40° C. and a humidity of 75% is preferably less than 45% and more preferably less than 43%.

The alginate aqueous solution preparation of the present invention can be used as a pharmaceutical or medical device. To be more specific, the usage include pharmaceuticals or medical device used for cartilage regeneration agents, cartilage disorder therapeutic agents, cartilage damage filling agents, intervertebral disk disorder therapeutic agents, meniscal disorder therapeutic agents, and the like. The alginate aqueous solution preparation of the present invention is one prepared to be ready-to-use, and can be diluted by addition of a solvent such as injection water or physiological saline for use as a solution having a concentration and viscosity suitable for the intended use. The solution can be used by impregnating a support such as a sponge with the solution. In addition, it is possible to use the solution gelated by addition of a cross-linking agent such as a solution of calcium chloride. In addition, it is possible to take the alginate aqueous solution of the present invention out of a container such as a vial and use the alginate aqueous solution directly or after dilution in the form of application or the like onto the diseased site.

Next, a preferable method of producing an alginate aqueous solution preparation of the present invention is described.

In other words, it is preferable to produce by a method of aseptically filtering an aqueous solution formed by dissolving (a) a monovalent metal alginate and (b) a salt selected from a monovalent metal salt and an ammonium salt, filling a container such as a vial, and then concentrating the aqueous solution by drying to a predetermined concentration.

In addition, production is also possible by aseptically filtering an aqueous solution formed by dissolving (a) a monovalent metal alginate and (b) a salt selected from a monovalent metal salt and an ammonium salt, filling a container such as a vial, and then aseptically condensing the freeze-dried one with water.

In addition, production is also possible by aseptically filtering an aqueous solution formed by dissolving (a) a monovalent metal alginate and (b) a salt selected from a monovalent metal salt and an ammonium salt, concentrating the aqueous solution by drying to a predetermined concentration, and then filling a container such as a vial or a syringe.

In addition, production is also possible by aseptically filtering an aqueous solution formed by dissolving (a) a monovalent metal alginate and (b) a salt selected from a monovalent metal salt and an ammonium salt and then filling a container such as a vial or a syringe.

To be more specific, an aqueous solution is prepared by dissolving the component (a) and the component (b) into injection water. Here, it is preferable that the concentration of the monovalent metal alginate being the component (a) be 0.1% by mass or more and 1.4% by mass or less, more preferably 0.2% by mass or more and 1.3% by mass or less, and further preferably, 0.3% by mass or more and 1.2% by mass or less. The salt being the component (b) is recommended to be used in such an amount that the mass ratio of the component (a)/the component (b) is 100/70 to 100/10 and more preferably 100/60 to 100/20 relative to the component (a) used. However, after the concentration by drying, it is important to adjust the concentration of the component (b) to 0.5 to 2% by mass. Although the component (a) and the component (b) can be added into water in any order, it is preferable to add in the order of the component (a) and the component (b). Dissolution is usually performed at room temperature, but in some cases the solution may be cooled, heated, or warmed to a temperature of about 40° C. In the dissolution, any type of stirrer may be used.

In the present invention, the viscosity (20° C.) of the aqueous solution into which the component (a) and the component (b) are dissolved is preferably 40 to 800 mPa·s. Here, as the viscosity of the aqueous solution, it is possible to use a value measured at 20° C. by use of a two-axis cylindrical metal cup in a rotational viscometer RheoStress RS600 (manufactured by Thermo Haake GmbH).

After dissolution, in the present invention, the aqueous solution is filtered, preferably aseptically filtered, to reduce the endotoxin level. Here, it is preferable to use a filtration filter such as a 0.22 um filter.

Note that the sterile preparation of the present invention means, for example, a preparation which conforms to the sterility testing method defined in the Japanese Pharmacopoeia.

The present invention may include filling a container such as a vial with the aqueous solution into which the component (a) and the component (b) are dissolved or with the aqueous solution formed by dissolving the component (a) and the component (b), and then concentrating the aqueous solution preferably under a non-oxidizing atmosphere such as in a nitrogen stream by drying in a usual manner such as reduced pressure drying or normal pressure drying such that the concentration of the monovalent metal alginate is 1.5% or more. Alternatively, the present invention may include concentrating the aqueous solution into which the component (a) and the component (b) are dissolved or the aqueous solution formed by dissolving the component (a) and the component (b) preferably under a non-oxidizing atmosphere such as in a nitrogen stream by drying in a usual manner such as reduced pressure drying or normal pressure drying such that the concentration of the monovalent metal alginate is 1.5% or more, and then filling a container such as a vial or a syringe with the aqueous solution. The container such as a vial or a syringe to be filled with the aqueous solution of monovalent metal alginate of the present invention preferably has a volume of 2 to 50 ml. In addition, the filling amount of the aqueous solution of monovalent metal alginate of the present invention is preferably about 1 to 90% of the volume of the container such as a vial or a syringe. For example, the filling amount of the alginate aqueous solution into the container is 2 to 50 ml. In addition, the filling amount of an alginate into the container is, as dry sodium alginate, 50 to 500 mg, preferably 50 to 150 mg, and more preferably 90 to 110 mg.

After the concentration or filling of the container is finished, it is preferable to replace the air in the container such as a vial with nitrogen gas, preferably dry nitrogen gas, and then to seal the container with a cap, a seal, or the like. The cap used for a vial or the like is preferably made of rubber, in particular bromobutyl rubber. Note that it is possible to use a vial made of various commercially available materials such as a glass vial. In addition, it is possible to coat the inner wall of the vial with, for example, silicone. The sealed container or the airtight container to be filled with the aqueous solution preparation of the present invention includes a vial, but it is also possible to use an ampoule, a syringe, a soft bag, or the like instead of a vial, and a vial or a syringe is preferable. In the case of using a syringe, it is ready-to-use as a pre-filled syringe, which is more convenient.

The present invention further provides a suppressant of viscosity decrease with the lapse of time for an alginate aqueous solution preparation of a monovalent metal alginate, which contains a salt selected from a monovalent metal salt and an ammonium salt. In addition, the present invention provides a method of suppressing viscosity decrease with the lapse of time of an alginate aqueous solution preparation of a monovalent metal alginate by incorporating a salt selected from a monovalent metal salt and an ammonium salt into an alginate aqueous solution preparation of a monovalent metal alginate.

In these aspects, it is preferable to use the component (b) being a salt selected from a monovalent metal salt and an ammonium salt such that the mass ratio of the component (a)/the component (b) is within the range of 100/70 to 100/10 and more preferably within the range of 100/60 to 100/20 relative to the component (a) being a monovalent metal alginate. Thus, it is possible to suppress viscosity decrease with the lapse of time of the aqueous solution preparation of a monovalent metal alginate.

The present invention also provides a method of stabilizing an aqueous solution preparation of a monovalent metal alginate which includes the step of aseptically filtering an aqueous solution formed by dissolving the component (a) and the component (b), followed by drying under a non-oxidizing atmosphere to concentrate the concentration of the monovalent metal alginate.

EXAMPLES

Next, the present invention is described in further detail by showing examples. However, the present invention is not limited to these examples.

Example 1

A sodium alginate aqueous solution preparation was prepared by the following method.
(1) Method of Preparing Aqueous Solution of Sodium Alginate Refined sodium alginate (purchased from KIMICA Corporation: ALG-1 (average molecular weight 250,000: measured by the GPC-MALS method: purity (quantitative value determined) 98%: viscosity (1% by mass solution, 20° C.) 525 mPa·s: M/G ratio 1.2), sodium chloride (manufactured by Merck & Co., Inc.), and water (injection water: manufactured by Otsuka Pharmaceutical Co., Ltd.) were used.

An aqueous solution having a sodium alginate concentration of 1% was prepared by charging a sterilized container having a volume of 1 to 2 L with refined sodium alginate and sodium chloride together with injection water, followed by stirring and dissolution at room temperature.

Figure 1:
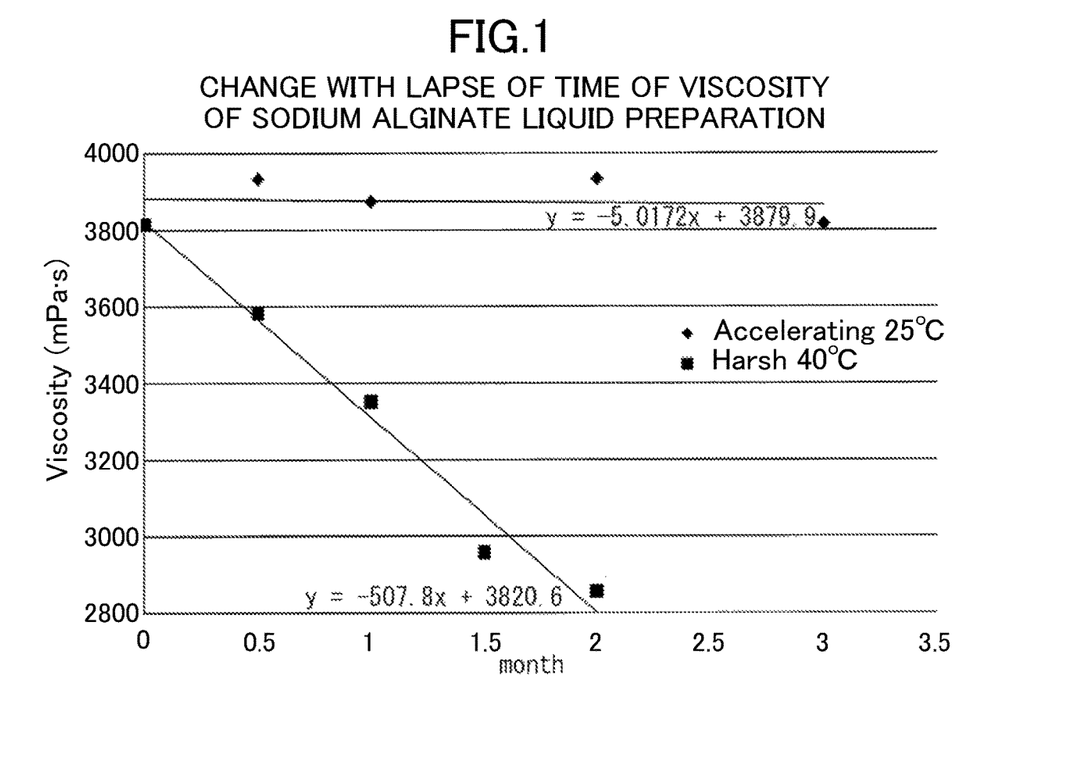
FIG. 1 is a diagram showing evaluation results of viscosity change with the lapse of time of an aqueous solution having a sodium alginate concentration of 2% by mass of the present invention at 25° C./60% RH (accelerating conditions) and 40° C./75% RH (harsh conditions).

Next, this prepared drug solution was subjected to aseptic filtration using a 0.22 µm filter (manufactured by Millipore) inside a clean bench.
(2) Concentration The prepared drug solution prepared by the above method was filling in a glass vial having a volume of 20 ml as a dry sodium alginate in an amount of 102 mg per vial and concentrated in a usual manner by use of a freeze-drying apparatus. After that, the air in the vial was replaced by dry nitrogen gas to form a sealed state using a cap. Thus, an aqueous solution preparation with 2% by mass of sodium alginate and 0.9% by mass of sodium chloride was prepared.
(3) Stability with Lapse of Time of Na Alginate Aqueous Solution Preparation For the purpose of evaluating the viscosity change with the lapse of time of the aqueous solution having a Na alginate concentration of 2% by mass obtained in (2) above, the aqueous solution was stored in constant temperature and humidity rooms of at 25° C. and 60% RH (accelerating conditions) and 40° C. and 75% RH (harsh conditions) to evaluate the viscosity change with the lapse of time.

Regarding the measurement of the viscosity, the measurement was performed on a viscosity at 20° C. for 3 minutes by use of a two-axis cylindrical metal cup in a rotational viscometer RheoStress RS600 (manufactured by Thermo Haake GmbH), and the measurement value employed was the average during the interval between 1 minute after the start and until 2 minutes after the start.
(4) Results FIG. 1 shows the obtained results.

From the results in FIG. 1, it was found that, at 25° C. (accelerating conditions), the stability may be secured in cold storage for 2 years because the viscosity decrease is gentle. In particular, it is found that the three-month viscosity decrease rate is less than 1% under the accelerating conditions of 25° C. and 60% RH. In addition, the three-month viscosity decrease rate was estimated to be about 40% from the result for 2 months at 40° C. and 75% RH.

Example 2

Sodium alginate aqueous solution preparations were prepared using sodium alginates with different molecular weights according to the method of Example 1.
(1) Method of Preparing Aqueous Solution of Sodium Alginate and Concentration Refined sodium alginates ALG-1 (same as Example 1) and ALG-2 (purchased from KIMICA Corporation: average molecular weight 150,000: measured by the GPC-MALS method) were used to prepare aqueous solution preparations with 2% by mass (ALG-1) and 3.5% by mass (ALG-2) of sodium alginate. The concentration of sodium chloride was 0.9% by mass in both cases.
(2) Stability with Lapse of Time of Na Alginate Aqueous Solution Preparation For the purpose of evaluating the viscosity change with the lapse of time of each of the Na alginate aqueous solutions obtained in (1), the aqueous solutions were stored in constant temperature and humidity rooms of 40° C. and 75% RH (harsh conditions) to evaluate the viscosity change with the lapse of time according to the method of Example 1.

(3) Results

Figure 2:
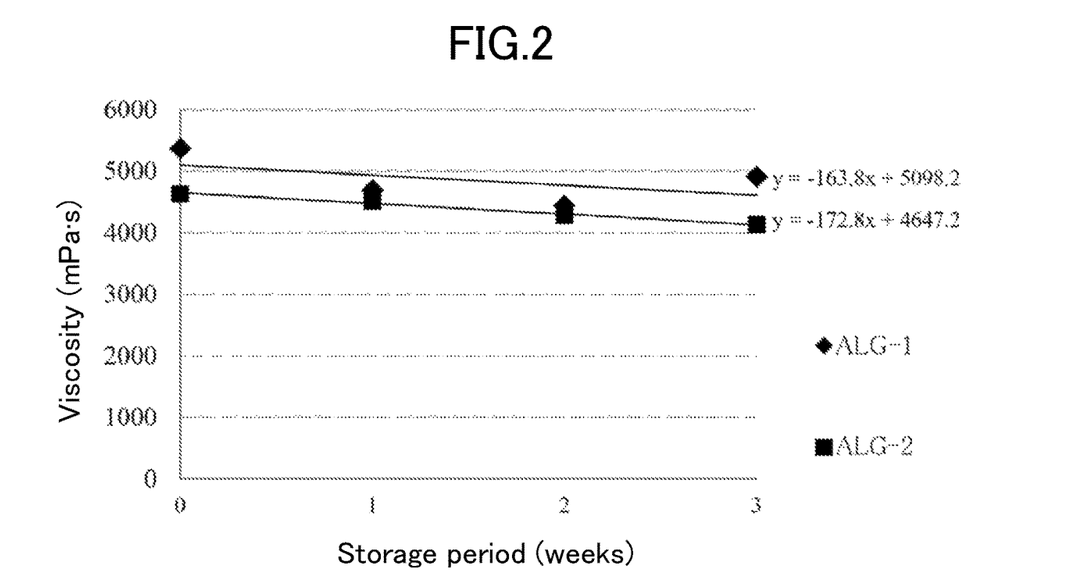
FIG. 2 is a diagram showing a viscosity decrease suppression effect of sodium chloride for storage at 40° C./75% RH of sodium alginate aqueous solution preparations with various molecular weights in Example 2.

FIG. 2 shows the obtained results.

From the results for harsh conditions in FIG. 2, it was found that the stability may be secured in cold storage for 2 years. In addition, it was found that the three-month viscosity decrease rates of ALG-1 and ALG-2 estimated from the results for 3 weeks in the harsh conditions of 40° C. and 75% RH were about 39% and about 45%, respectively.

Example 3

Various freeze-dried sodium alginate preparations were prepared by the following method, and then aseptically reconstituted with water to form sodium alginate aqueous solution preparations, which were measured and evaluated in terms of viscosity with the lapse of time according to the method of Example 1.

(1) Method of Preparing Aqueous Solution of Sodium Alginate

The same refined sodium alginate, sodium chloride (manufactured by Merck & Co., Inc.), and water (injection water: manufactured by Otsuka Pharmaceutical Co., Ltd.) as those used in Example 1 were used.

A raw drug solution to be used was prepared by filling a sterilized container having a volume of 1 to 2 L with refined sodium alginate alone (sodium alginate 5.1 g/L) or refined sodium alginate and sodium chloride (sodium alginate 5.1 g/L: NaCl 2.25 g/L) together with injection water, followed by stirring and dissolution at room temperature.

Next, the raw drug solution to be used was subjected to aseptic filtration using a 0.22 μm filter (manufactured by Millipore) inside a clean bench and was filled in a glass vial having a volume of 20 ml as a dry sodium alginate in an amount of 102 mg per vial.

(2) Freeze-Drying

A glass vial filled with a sodium alginate aqueous solution was freeze-dried in the following conditions by use of a freeze-drying apparatus.

Freezing and drying conditions: it took 270 minutes for cooling to −40° C. and complete freezing was performed at this temperature for 600 minutes of retention. After that, it took 240 minutes for rising the temperature to −10° C. At this temperature, pressure was reduced so that the pressure inside the housing of the freeze-dryer was 3 Pa or less, followed by retention for about 120 hours to perform drying to make the water content about 2% by mass.

After the freeze-drying, the air of the vial was replaced by dry nitrogen gas and then a tightly sealed state was formed using a cap. The resultant was provided for the following test.

(3) Stability with Lapse of Time of Solution with 2% by Mass of Sodium Alginate

The freeze-dried sodium alginate product obtained in (2) above was dissolved in water (injection water: manufactured by Otsuka Pharmaceutical Co., Ltd.) to prepare the following aqueous solutions 1 and 2 having a sodium alginate concentration of 2% by mass. In addition, a freeze-dried product with refined sodium alginate alone was dissolved in physiological saline to prepare an aqueous solution 3 having a sodium alginate concentration of 2% by mass.

aqueous solution 1: with NaCl during freeze-drying: reconstituted with injection water (Example 3-1)

aqueous solution 2: without NaCl during freeze-drying: reconstituted with injection water (Reference Example 3-2)

aqueous solution 3: without NaCl during freeze-drying: reconstituted with physiological saline (Reference Example 3-3)

For these solutions with 2% by mass of sodium alginate, the stability with the lapse of time at 40° C./75% RH, at 25° C./60% RH, and at 2 to 8° C. was evaluated in terms of viscosity change with the lapse of time. The viscosity was measured by the same method as Example 1.

Figure 3:
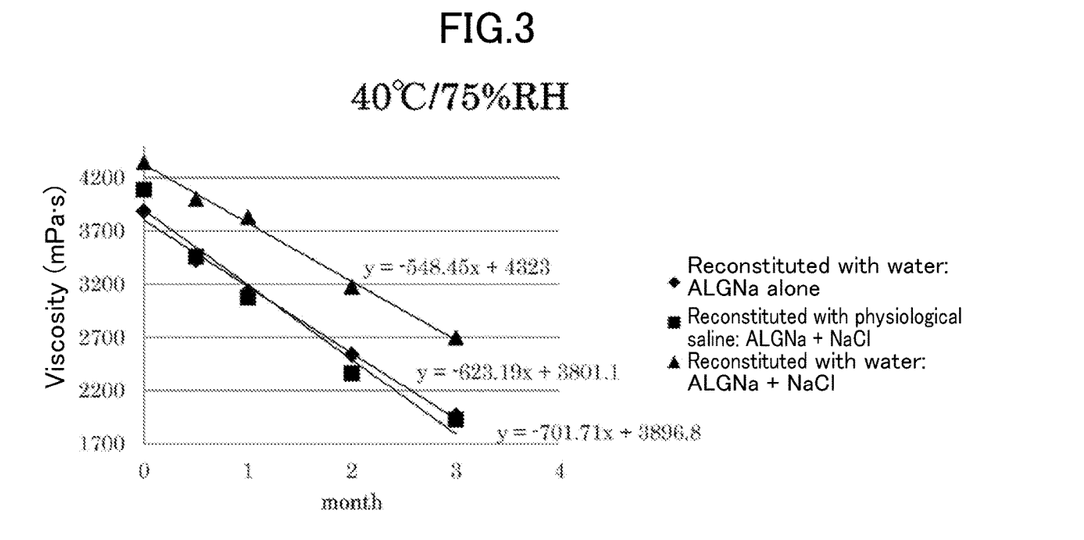
FIG. 3 is a diagram showing a viscosity decrease suppression effect of sodium chloride for storage at 40° C./75% RH in Example 3.
Figure 4:
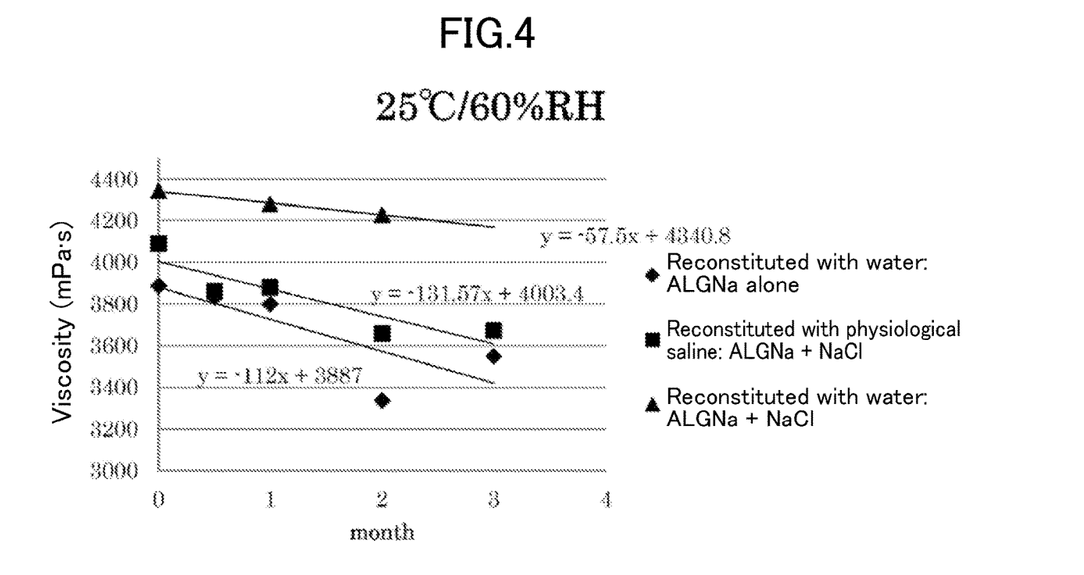
FIG. 4 is a diagram showing a viscosity decrease suppression effect of sodium chloride for storage at 25° C./60% RH in Example 3.
Figure 5:
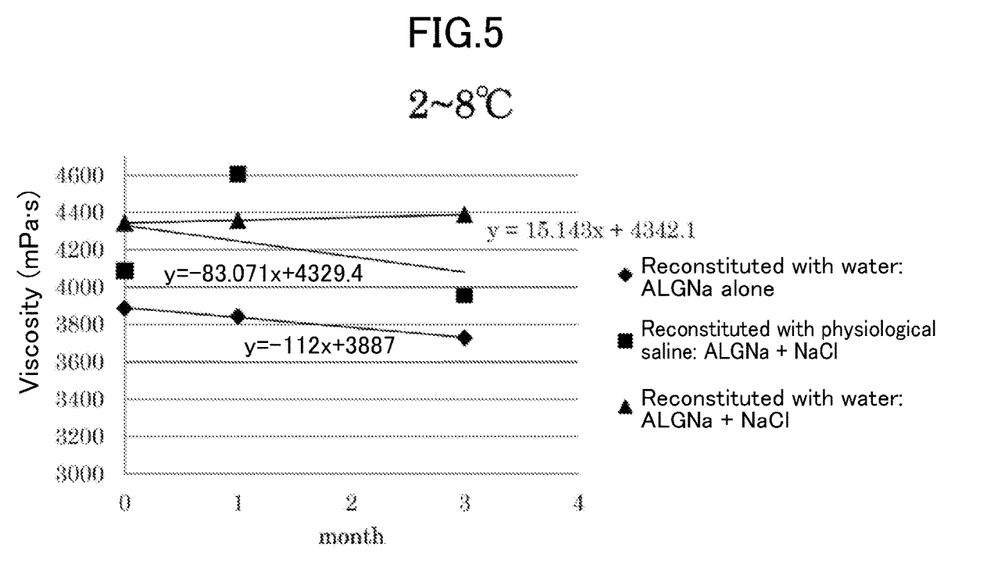
FIG. 5 is a diagram showing a viscosity decrease suppression effect of sodium chloride for storage at 2 to 8° C. in Example 3.

FIG. 3 to FIG. 5 show the obtained results.

It is found from the results in FIG. 3 that the presence of NaCl during freeze-drying makes the viscosity decrease gentle (aqueous solution 1: Example 3-1: gradient of the viscosity decrease -548, three-month viscosity decrease rate about 38%), making it possible to suppress the viscosity decrease over time. Conversely, it is found that the absence of NaCl during freeze-drying makes the viscosity decrease over time large (aqueous solution 2: Reference Example 3-2: gradient of the viscosity decrease −623, three-month viscosity decrease rate about 49%) and that it is impossible to suppress the viscosity decrease over time even when NaCl is absent during freeze-drying and added thereafter (aqueous solution 3: Reference Example 3-3: gradient of the viscosity decrease −702, three-month viscosity decrease rate about 54%). Note that it is found the preparation of Example 3-1 has a three-month viscosity decrease rate of less than 47% under the conditions of 40° C. and 75% RH.

It is also found from the results of FIG. 4 that the presence of NaCl during freeze-drying makes it possible to suppress the viscosity decrease over time, that the absence of NaCl during freeze-drying makes the viscosity decrease over time large, and that it is impossible to suppress the viscosity decrease over time even when NaCl is absent during freeze-drying and added thereafter. Note that it is found the preparation of Example 3-1 has a three-month viscosity decrease rate of less than 7% under the conditions of 25° C. and 60% RH.

It is also found from the results of FIG. 5 that the presence of NaCl during freeze-drying makes it possible to suppress the viscosity decrease over time, that the absence of NaCl during freeze-drying makes the viscosity decrease over time large, and that it is impossible to suppress the viscosity decrease over time even when NaCl is absent during freeze-drying and added thereafter. Note that it is found the preparation of Example 3-1 has a three-month viscosity decrease rate of less than 3% under the storage condition of 2 to 8° C.

Example 4

The stability with the lapse of time of the solution with 2% by mass of sodium alginate prepared in Example 3-1 (aqueous solution 1) at 25° C./60% RH and at 2 to 8° C. until month 18 was evaluated in terms of viscosity change with the lapse of time. The viscosity was measured by the same method as Example 1.

Figure 6:
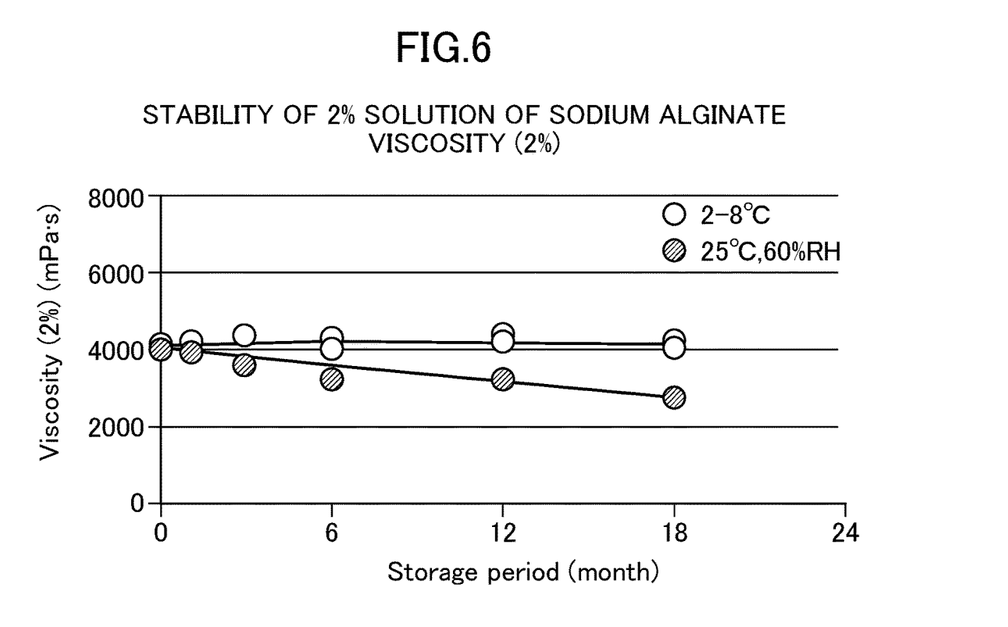
FIG. 6 is a diagram showing viscosity change with the lapse of time for long-term storage of 25° C./60% RH storage and 2 to 8° C. storage of a sodium alginate aqueous solution preparation of the present invention in Example 4.

FIG. 6 shows the obtained results.

It was confirmed from the results in FIG. 6 that, when NaCl is present during freeze-drying, the aqueous solution preparation after being reconstituted with water is stable for a long period of time. It is found from the results of the test that, in the preparation of Example 3-1, the average three-month viscosity decrease rate under the condition of 25° C. and 60% RH is about 6% and less than 7%. In addition, the preparation of Example 3-1 experiences no substantial viscosity decrease for 18 months under the storage condition of 2 to 8° C., and has an average three-month viscosity decrease rate of less than about 3%.

Example 5

An infusion bag having a volume of 5 L was aseptically filled with 1.6 kg of the prepared drug solution prepared and aseptically filtered in (1) of Example 1. Dry nitrogen gas was allowed to flow in the infusion bag, and concentration was performed under atmospheric pressure while heating and stirring appropriately in a clean bench to obtain a prepared drug solution with 2% by mass of sodium alginate and 0.9% by mass of sodium chloride (lot 1). A prepared drug solution was obtained in the same manner as described above except that the heating conditions were changed (lot 2). This solution was aseptically filled in a glass vial having a volume of 20 mL, which was sealed with a cap to obtain a sodium alginate aqueous solution preparation. Separately, the solution was aseptically filled in a syringe having a volume of 20 mL, which was sealed with a cap to obtain a pre-filled syringe filled with a sodium alginate aqueous solution preparation. Here, the operation of aseptic filling was performed in a clean bench.

For the above-described vial-filled solutions with 2% by mass of sodium alginate (lot 1 and lot 2), the stability with the lapse of time at 40° C./70% RH until month 2 was evaluated in terms of viscosity change with the lapse of time. The viscosity was measured by the same method as Example 1.

Figure 7:
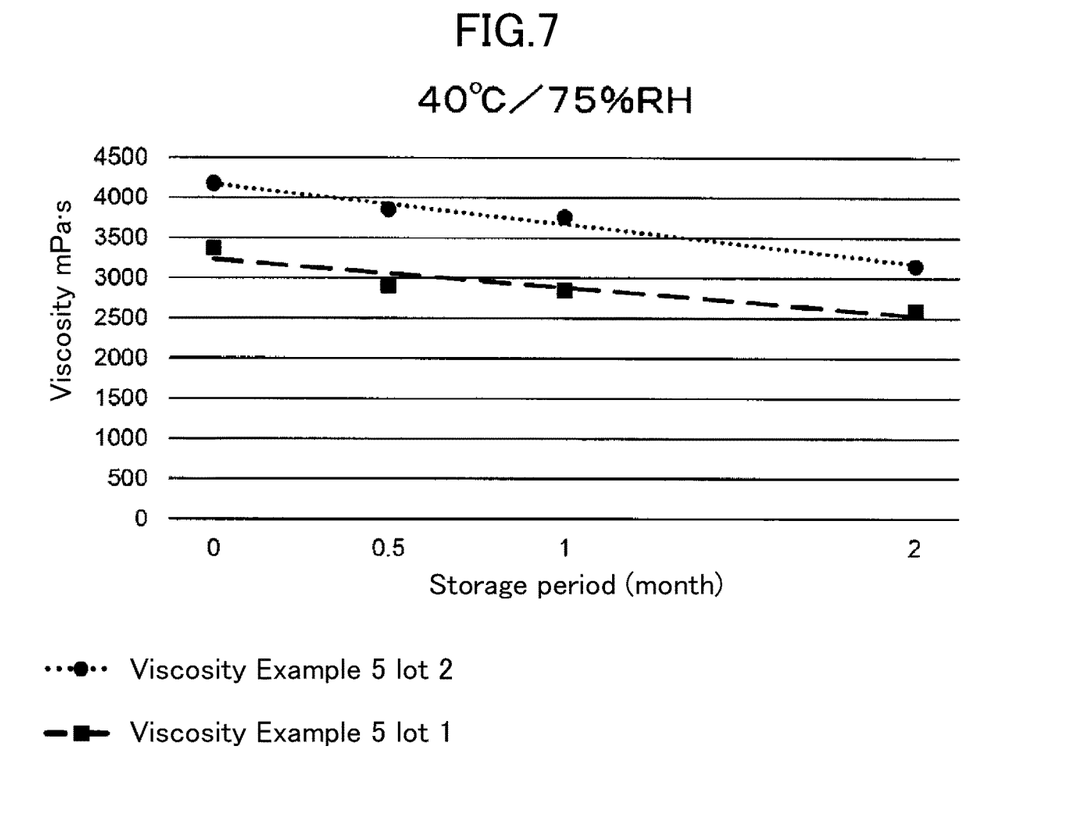
FIG. 7 is a diagram showing viscosity change with the lapse of time for long-term storage of 40° C./75% RH storage of a sodium alginate aqueous solution preparation of the present invention in Example 5.

FIG. 7 shows the obtained results.

It was revealed from the results in FIG. 7 that the three-month viscosity decrease rates of the preparations of Example 5 (lot 1 and lot 2) estimated from the results for 2 months at 40° C. and 75% RH were about 35% and about 37%, respectively, which were the same stability as that of the aqueous solution preparation reconstituted with water after freeze-drying.

What is claimed is:

1. A ready-to-use sterile alginate aqueous solution preparation which is packed in a sealed container or an airtight container and which has storage stability, consisting essentially of the following components (a) to (c):
    (a) monovalent metal salt of alginic acid having a weight average molecular weight of 50,000 to 400,000 by a GPC-MALS method wherein the monovalent metal salt of alginic acid has less than 100 EU/g of an endotoxin value measured by the endotoxin test conforming to the Japanese Pharmacopoeia, and wherein said alginic acid has a M/G ratio of 0.8 to 1.6;
    (b) a salt selected from a monovalent metal salt and an ammonium salt; and
    (c) water, wherein
    a concentration of the component (a) is 1.5% to 7% by mass,
    a concentration of the component (b) is 0.5 to 2% by mass, and
    a viscosity measured at 20° C. using a rotational viscometer is 2700 mPa·s or more.

2. The alginate aqueous solution preparation according to claim 1, wherein the salt selected from a monovalent metal salt and an ammonium salt of the component (b) is sodium chloride.

3. The alginate aqueous solution preparation according to claim 1, wherein the sealed container or the airtight container is a vial.

4. The alginate aqueous solution preparation according to claim 1, wherein a three-month viscosity decrease rate of the preparation having storage stability satisfies any of
    1) Less than 3% in a case of storage at 2 to 8° C.,
    2) less than 7% in a case of storage at 25° C., and
    3) less than 47% in a case of storage at 40° C.

5. The alginate aqueous solution preparation according to claim 1 for use as a pharmaceutical or medical device.

6. The alginate aqueous solution preparation according to claim 1, wherein a volume of the sealed container or the airtight container is 2 to 50 ml.

7. The alginate aqueous solution preparation according to claim 1, wherein air in the sealed container or the airtight container is replaced by nitrogen gas.

8. A method of producing the alginate aqueous solution preparation according to claim 1, comprising:
    sterically or aseptically filtering an aqueous solution of a monovalent metal alginate containing a salt selected from a monovalent metal salt and an ammonium salt, filling a container with the filtrate, followed by sealing after concentrating the filtrate or after freeze-drying the filtrate and aseptically reconstituting the freeze-dried one with water.

9. A method of producing the alginate aqueous solution preparation according to claim 1, comprising:
    sterically or aseptically filtering an aqueous solution of a monovalent metal alginate containing a salt selected from a monovalent metal salt and an ammonium salt;
    concentrating the filtrate; and
    aseptically filling the concentrated filtrate into a container, followed by sealing.

10. The alginate aqueous solution preparation according to claim 1, wherein the sealed container or the airtight container is a pre-filled syringe.

11. The alginate aqueous solution preparation according to claim 1, which meets any one of the following [1] to [3]:
    [1] the component (a) has an average molecular weight by the GPC-MALS method of 250,000, and has the concentration of 1.5% by mass to 3% by mass,
    [2] the component (a) has an average molecular weight by the GPC-MALS method of 150,000, and has the concentration of 2% by mass to 5% by mass, or
    [3] the component (a) has an average molecular weight by the GPC-MALS method of 72,000, and has the concentration of 3% by mass to 7% by mass.

* * * * *